(12) United States Patent
Nimocks

(10) Patent No.: US 9,040,068 B2
(45) Date of Patent: May 26, 2015

(54) CONTROL OF BED BUGS

(75) Inventor: David Nimocks, Fayetteville, NC (US)

(73) Assignee: ENSYSTEX INC., Fayetteville, NC (US)

( * ) Notice: Subject to any disclaimer, the term of this patent is extended or adjusted under 35 U.S.C. 154(b) by 0 days.

(21) Appl. No.: 13/466,025

(22) Filed: May 7, 2012

(65) Prior Publication Data

US 2012/0294922 A1     Nov. 22, 2012

Related U.S. Application Data

(60) Provisional application No. 61/488,715, filed on May 21, 2011.

(51) Int. Cl.
     *A01N 41/10*      (2006.01)
     *A01N 51/00*      (2006.01)

(52) U.S. Cl.
     CPC ............. *A01N 51/00* (2013.01); *A01N 2300/00* (2013.01); *A01N 41/10* (2013.01)

(58) Field of Classification Search
     CPC ... A01N 2300/00; A01N 51/00; A01N 25/02; A01N 25/08
     USPC ............ 424/409; 428/343, 354; 514/708, 341
     See application file for complete search history.

(56) References Cited

U.S. PATENT DOCUMENTS

| | | | | |
|---|---|---|---|---|
| 7,687,533 | B2 * | 3/2010 | Critcher et al. | 514/407 |
| 7,743,552 | B2 | 6/2010 | Borth et al. | |
| 7,905,048 | B2 | 3/2011 | Borth et al. | |
| 8,404,260 | B2 * | 3/2013 | Reid et al. | 424/405 |
| 2010/0093532 | A1 * | 4/2010 | Voeste et al. | 504/100 |

OTHER PUBLICATIONS

Kaushik et al; Title:Percutaneous penetration modifiers and formulation effects , International Journal of Pharmaceutics, vol. 386, Issues 1-2, 15, pp. 42-51, published Feb. 2010.*

* cited by examiner

*Primary Examiner* — Ali Soroush
*Assistant Examiner* — Yanzhi Zhang
(74) *Attorney, Agent, or Firm* — Hultquist, PLLC; Steven J. Hultquist; Mary B. Grant

(57) ABSTRACT

A method of combating bed bugs and/or other insects in a locus containing or susceptible to presence of same, in which a DMSO-containing formulation is applied to the locus. Various pesticidal compositions are disclosed as useful for such purpose, including compositions in which DMSO is in combination with an alcohol and/or another pesticidal active agent. Compositions of the disclosure can be applied to a variety of loci, to effectively eradicate bed bugs for extended periods of time.

7 Claims, No Drawings

CONTROL OF BED BUGS

CROSS REFERENCE TO RELATED APPLICATION

This application claims the benefit under 35 U.S.C. §119 of U.S. Provisional Patent Application No. 61/488,715 filed May 21, 2011 in the name of David Nimocks. The disclosure of U.S. Provisional Patent Application No. 61/488,715 is hereby incorporated herein by reference in its respective entirety, for all purposes.

FIELD

The present disclosure relates to control of bed bugs, and more specifically to compositions and methods for combating such pests.

DESCRIPTION OF THE RELATED ART

Cimicidae or bed bugs (Phylum Arthropoda, Class Insecta, Order Hemiptera, Family Cimicidae—most common type, *Cimex lectularius* L.) are small, oval, flat, parasitic, reddish-brown, wingless insects. Cimicidae feed on the blood of warm-blooded mammals, including humans as well as other animals. They molt five times before reaching maturity and require at least one blood feeding between each molt. Cimicidae often survive up to two months without food, but can under certain circumstances live a year or more without feeding. Cimicidae live in close proximity to their food sources, and remain ready to opportunistically feed on their hosts. Cimicidae are primarily nocturnal and emerge normally at night when their food source is sleeping and immobile. After feeding, they return to hiding in proximity to their food source, e.g., within cracks and crevices in nearby structures, or in mattresses or other bedding articles.

In many instances the only evidence of the presence and/or feeding of Cimicidae are allergic welts on the skin of their victims and/or faint streaks of blood left as they retreat across surfaces, such as bed linens, to their hiding places. A number of health effects may occur due to Cimicidae, including, without limitation, skin rashes, psychological effects, and allergic symptoms (e.g., asthmatic reactions). Cimicidae bites or cimicosis may lead to a range of skin manifestations from minimal effects to prominent blisters.

Although Cimicidae are not known to be deadly or to be vectors for serious disease, most persons aware of these pests find the prospect of having their blood involuntarily sucked, e.g., in the middle of the night, profoundly repugnant.

Most persons who discover they are living in domiciles infested with bed bugs, are, based on their disgust as to the possibility they may be unwittingly serving as a current or subsequent opportunistic food source for a bed bug population, highly motivated to eradicate such pests. Bed bugs are, however, by far one of the most difficult household pests to eradicate.

In the developed world, Cimicidae were largely eradicated as pests in the early 1940s. They have, however, increased in prevalence since about 1995, and currently have increased in size of populations and frequency of emergence to such extent as to be a subject of widespread concern.

While the exact causes of this resurgence remain unclear, it is variously ascribed to greater foreign travel, more frequent exchange of second-hand furnishings, a neglect of focus on bed bug countermeasures, and increasing resistance of bed bugs to pesticides. One hypothesis concerning the resurgence is that older, more persistent, and now banned pesticides (insecticides) that were at one time effective against bed bugs have been removed from the market in favor of pesticides that are less environmentally persistent (with respect to their environmental degradation) but that are also less effective against bed bugs.

Concerning existing pesticides, those that are effective against most types of insects are almost universally less than 100% effective against bed bugs. Even if somewhat effective, these existing pesticides typically require long periods of time in which to be effective (cidal) against bed bugs.

These characteristics appear to be due to repeated exposure of successive generations of fast-breeding bed bugs to a wide range of pesticides possessing a wide range of different modes of action, i.e., mechanisms for killing bed bugs. As a result, successive generations of bed bugs have developed immunity in response to such exposures, with natural selection producing bed bugs that have highly evolved resistance characteristics to such pesticides, including an innate ability to detoxify these pesticidal agents at concentrations up to the levels at which such pesticides become cidally effective.

Bed bugs develop resistance to various pesticides, regardless of their mode of action, in an extremely rapid fashion. As a result, pesticides used for bed bug eradication rapidly diminish in effectiveness, as successive generations of rapidly reproducing bed bugs are exposed to such pesticides and rapidly acclimate to them. Such rapid acquisition of resistance to many modern and currently used insecticidal active ingredients may be linked to residual or inherent resistance to long-banned insecticides such as DDT. In any event, bed bug insecticide resistance is currently increasing at what almost seems to be an accelerating rate.

It would be an important and welcome development to render currently available pesticides more effective against bed bugs, since it appears that no matter how new and powerful pesticidal agents may be to insect pests generally, or to bed bugs themselves initially, bed bugs will quickly adapt and acquire immunity to such agents, particularly when they are applied in a conventional manner.

Many non-pesticidal (e.g., non-toxicant-based) insect control methods have been proposed as an alternative to pesticidal treatment methods, for containment and eradication of bed bugs. Some alternative bed bug control methods can be effective when carried out with a high degree of precision and care. These alternative approaches include use of heat, steam, cold, frost, attraction and entrapment, to contain and eradicate bed bugs. While these methods are not susceptible to bed bug adaptation and development of resistance to them, such methods do have the deficiency that while they are effective in the first instance, they offer no residual effect.

Further, it is often difficult to utilize and direct these methods against bed bug infestations. For example, heat and cold, while useful as bed bug control methods, are difficult to selectively focus or concentrate throughout a large area medium that is infested or susceptible to infestation by bed bugs, so that all bed bugs in such locus are reliably eradicated. Still further, some methods, such as heat, can damage surfaces, structures or articles to which they are applied. Another problem in bed bug eradication resides in the fact that bed bugs forage for blood meals only at certain times, spending the balance of their time in protected habitats, which makes their detection, much less their eradication, highly problematic.

Time is particularly critical in the effort to eradicate bed bugs, not only because persons in countering bed bug infestation desire extremely rapid and effective methods of eradication, but also because treatment agents conventionally available have limited time-frames of effectiveness. For example, toxicant-based extermination methods are extremely effective and rapid in the case of poisonous gas fumigation, and it is desirable to minimize the period of time that such poisonous gas is used, to correspondingly minimize the potential for hazardous exposure to persons in or around the premises being fumigated. Such fumigation methods also have the deficiency of being costly and inconvenient, as well as requiring considerable preparation time for the fumigation operation, to ensure its safety.

Direct application of toxicant-containing pesticide formulations to bed bugs and surfaces that they inhabit may be carried out with liquid or dust formulations. Liquid formulations are generally suspension concentrates or emulsion concentrates, containing one or more insecticidal active ingredients, with the concentrate being diluted with water or other liquid medium to prepare the final composition for use. Dust formulations may be constituted with active pesticidal ingredients mixed with talc or other powdered form carrier medium. Liquid formulations are typically applied by spraying or aerosolization, while dust and powder formulations are typically applied with dusting equipment.

In such application of toxicant-containing pesticidal formulations, there is wide variability in the "time to effectiveness" and in overall efficacy of the different active ingredients against bed bugs, dependent on the mode of action of the specific toxicant employed, the type of formulation in which the toxicant is applied, the specific application method utilized for the toxicant-containing formulation, the character of the formulation once it is applied, and whether the formulation is applied directly to the bed bugs or is indirectly applied to such pest, e.g., by application of the formulation to a surface, material or article that the bed bugs are expected to inhabit in the near term.

Given these considerations, the speed of effectiveness and overall effectiveness of pesticidal formulations against bed bugs will depend on several specific factors.

Of primary importance is the inherent effectiveness of the toxicant (pesticidal active ingredient) against bed bugs. In this respect, there may be significant variability of effectiveness of the same toxicant when applied to different populations of bed bugs, due to physiological variations and varying levels of resistance within various populations against which the toxicant-containing formulation is used.

Further, assuming that a reasonably effective toxicant is selected to which a specific bed bug population is susceptible, the ultimate speed of action of the toxicant is ultimately dependent on the bioavailability, i.e., biological availability, of the toxicant in combating the biological processes of the bed bugs against which the toxicant-containing formulation is employed.

The level of bioavailability to bed bugs of a toxicant depends on the efficiency of the route of exposure of the toxicant-containing formulation to the biological processes of the bed bugs. The better and more efficient the route, the correspondingly more bioavailable is the toxicant, and, generally speaking, the faster it will act on the bed bug. Thus, any improvement that multiplies or accelerates the bioavailability of the pesticidal active ingredient to bed bugs has the potential to significantly speed its toxic action and increase its overall efficacy.

As previously discussed, a particular deficiency of conventional pesticidal formulations used against bed bugs relates to their lack of persistence, i.e., circumstance in which a pesticidal formulation applied to surfaces or areas that are presently or prospectively traversed by bed bugs will rapidly become ineffective as the applied composition rapidly degrades.

Further, the nature of bed bug infestation and the mode of action employed by bed bugs to attack their victims present inherent difficulties to achievement of effective bed bug control. Because the sole source of bed bug nutrition is extraction of blood from a host by sucking action of individual insects, bait or formulations designed for ingestion are not practical. Further, contact methods involving application of toxicant-containing formulations to surfaces, materials or articles that are or will be contacted by bed bugs must contend with bed bug body structure including a chitin-containing exoskeleton that forms a protective structure for the body of the bed bug.

Apart from the foregoing, pesticidal powders or dusts are problematic when used in living quarters or other premises in which the presence of powder or dust pesticides are problematic from the perspective of potential exposure to or ingestion by humans and/or other animals in such environments. Liquid formulations, while more amenable to application in such environments, e.g., by spraying, dipping, aerosol and other liquid administration techniques, have the associated disadvantages of markedly reduced efficacy when the liquid formulation dries or is absorbed by the surface or material to which it is applied, and the fact that the chitinous exoskeleton of bed bugs poses a significant barrier to making the pesticidal active ingredient bioavailable to the bed bugs so as to eradicate them quickly and effectively.

In consequence of the foregoing, there is a compelling need in the art for improved compositions and methods for eradicating bed bugs.

SUMMARY

The present invention relates to methods and compositions for control of bed bugs, which are cidally effective to achieve eradication of bed bugs in a locus containing or susceptible to incursion of bed bugs.

In one aspect, the invention relates to a method of combating bed bugs in a locus containing or susceptible to incursion of same, said method comprising applying to said locus and/or bed bugs therein a cidally effective amount of a formulation comprising dimethyl sulfoxide (DMSO).

Another aspect of the disclosure relates to a method of eradicating insects in a locus containing or susceptible to incursion of same, said method comprising applying to said locus and/or insects therein a cidally effective amount of a formulation comprising dimethyl sulfoxide (DMSO).

A further aspect of the disclosure relates to a pesticidal composition comprising dimethyl sulfoxide (DMSO) and at least one of: (i) insecticidal ingredient(s) and (ii) diluent(s).

Yet another aspect of the disclosure relates to an absorbent article comprising an absorbent body and DMSO absorbed on and/or in said absorbent body.

Other aspects, features and embodiments of the invention will be more fully apparent from the ensuing disclosure and appended claims.

DETAILED DESCRIPTION

The present disclosure is directed to compositions and methods for control of bed bugs, by which bed bugs can be eradicated in a locus containing or susceptible to incursion of bed bugs, in a safe, simple and effective manner.

The disclosure in various embodiments relates to pesticidal formulations that are effective in eradicating bed bugs, and to appertaining methods of utilizing same in the treatment of a locus infected with or susceptible to infection with bed bugs.

The compositions and methods of the present disclosure enable pesticidal agents effective for eradication of bed bugs to be applied to such insects or to environments in which they are or may be present, to rapidly kill bed bugs.

It is noted that as used herein and in the appended claims, the singular forms "a", "and", and "the" include plural referents unless the context clearly dictates otherwise.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention. The invention is described herein in various embodiments, and with reference to various features and aspects of the invention. The invention contemplates such features, aspects and embodiments in various permutations and combinations, as being within the scope of the invention. The invention may therefore be specified as comprising, consisting or consisting essentially of, any of such combinations and permutations of these specific features, aspects and embodiments, or a selected one or ones thereof.

Compositions of the present disclosure may variously comprise a liquid carrier, solvent, or diluent in a liquid-form insecticidal formulation that is effective against bed bugs, in which the liquid carrier, solvent or diluent evaporates slowly after application, thereby increasing the length of time that the formulation remains in place as a liquid after application. This in turn increases the likelihood that the toxicant will be transferred to the bed bug by contact of the formulation with bed bugs. Further, the carrier, solvent or diluent utilized in such bed bug-combating formulations, in addition to increasing the length of time during which the formulation is effective, also enhances penetration of the insecticidal active ingredient through the bed bug chitinous exoskeleton so that it is highly bioavailable to the bed bug, and accelerates the speed of cidal action of the formulation against the bed bug pest.

More specifically, the present disclosure reflects the discovery that the compound dimethyl sulfoxide (CAS#67-68-5), hereafter referred to as DMSO, when included in a liquid insecticide formulation containing insecticidal active ingredient(s), retards the rate of evaporation of the liquid formulation, thereby enhancing the bioavailability of the active ingredient(s) of the formulation to the bed bug, as well as increasing the penetration of the insecticidal active ingredient(s) through the bed bug chitin-containing exoskeleton. In this respect, it has been found that the inclusion of DMSO in a bed bug insect formulation greatly increases the speed of action of the formulation against bed bugs, as compared to the speed of action of a corresponding insect formulation not containing DMSO. Such increase in the speed of action is consistent with improvement in the bioavailability of the insecticidal active ingredient(s) to the bed bug attributable to the presence of DMSO in the formulation.

DMSO is an organosulfur compound and is a colorless liquid at room temperature conditions. It is a polar aprotic solvent and is miscible or soluble in a wide variety of organic compounds, in addition to being soluble in water. DMSO also exhibits a low toxicity in exposure to humans and animals, even when applied directly to a subject's skin. The slow rate of evaporation of DMSO (as compared to other liquid media such as water) is to due to the high boiling point (198° C.) of DMSO, and its high melting point of 19° C.

The inclusion of DMSO as a carrier, solvent or diluent in an insecticidal formulation results in an increase in the amount of time, after application of the formulation to a surface, material or article, in which the liquid component of the formulation remains in place at the application site, as compared to bed bug-combating formulations that utilize low boiling point diluents, solvents, or carriers that evaporate much more quickly.

DMSO-containing insecticidal formulations of the present disclosure remain available in liquid form for comparatively long periods of time after application, and are effective to transfer the formulation to the body of the bed bug, for absorption through the bed bug exoskeleton subsequent to contact of a bed bug with a surface, material or article to which the formulation has been applied.

Depending on the specific temperature of the application site, the applied DMSO in the DMSO-containing insecticidal formulation will remain in place in liquid form for a substantial length of time, remaining "wet to the touch," e.g., for several days to a week in duration. Once the liquid DMSO present on the application site evaporates, a waxy residue is left on the treated site. This waxy residue is also persistent in character and remains on the application surface or structure to which it is applied until it dissipates over a period of additional days, by gradual sublimation, leaving behind the residual insecticidal active ingredient of the DMSO-containing insecticidal formulation.

The precise mechanism of enhancement of the toxicity of insecticidal formulations containing DMSO, and the extended transfer availability (ability of the DMSO-containing insecticidal formulation to transfer to the bed bug body over an extended period of time) that is made possible by DMSO in the DMSO-containing insecticidal formulation remaining in liquid form, is not fully understood. Nonetheless, while not intending to be bound by any specific mechanism or explanation of such effect or efficacy, it is hypothesized that DMSO in formulations of the present disclosure solvates the insecticidal active ingredient in the formulation, so that the insecticidal active ingredient is presented to the bed bug body after the bed bug contacts a surface on which the formulation has been applied, in a form that is particularly effective to penetrate the chitinous exoskeleton. In other words, the DMSO may in such manner facilitate an increase in the bioavailability of the transferred active insecticidal ingredient(s) in the formulation, so that it is particularly cidally effective. At the same time, the DMSO in the formulation, by its particularly effective solvating character and high boiling point, maintains the formulation in a persisting "wet" state that enhances its ability to maintain cidal action for an extended time.

DMSO-containing insecticidal formulations of the present disclosure can take a wide variety of forms. Since many currently available insecticidal active ingredients are at least partially soluble in DMSO, it is possible to formulate a highly effective bed bug-combating pesticidal composition as a solution or suspension of the insecticidal active ingredient(s) that is/are solubilized or suspended in DMSO. Such formulations are highly effective in combating bed bug infestation and evidence sustained longevity after application, and may comprise, consist or consist essentially of DMSO and insecticidal active ingredient(s), as a liquid formulation that can be readily sprayed, aerosolized or otherwise applied by dipping, roller coating, or other application method, to surfaces, materials and articles in an environment containing or susceptible to incursion of bed bugs.

It has been found that in insecticidal formulations of the present disclosure, DMSO will persist, particularly on cool surfaces, materials and articles after application, for extended periods of time, consistent with sustained activity of the formulation. Effective amounts and rates of application can be substantially widely varied in the broad practice of the present disclosure, and specific concentrations of DMSO and active insecticidal ingredient(s) and efficacious rates of application can be readily determined, within the skill of the art, based on the disclosure herein, by the simple expedient of varying relative concentrations of DMSO and active insecticidal ingredient(s) and applying same at varied application rates to environments containing bed bugs and/or to which bed bugs are subsequently introduced, with monitoring of the cidal effects and activities of the variously applied and variously constituted DMSO-containing formulations. By such empirical determinations, specific formulations can be constituted for particular application environments, to achieve a highly effective formulation that is adapted for specific end use.

DMSO-containing insecticidal formulations of the present disclosure can be applied to exposed or hidden surfaces, or otherwise introduced to a locus containing or subject to incursion of bed bugs. Such surface application for example may involve dispensing of the liquid formulation onto the surface to an extent that the applied film of liquid material appears "wet" or shiny in character, evidencing continuous or near-continuous coverage of the surface that ensures the persisting availability of the applied formulation for an extended period of time, to maximize the potential contact of the formulation with bed bugs traversing such surface.

In some embodiments of the present disclosure, DMSO may be employed in combination with other solvents, carriers and/or diluents, to constitute the DMSO-containing insecticidal formulation for combating bed bugs. For example, DMSO can be used in combination with lower boiling point diluents such as water, alcohols, ketones, aldehydes, ethers, polyols and the like, the specific formulation depending on the desired character and ultimate administration method for applying the formulation to the bed bug environment. Thus, the formulation may be constituted to achieve a specific density, viscosity, volatility, etc., appropriate to the desired application.

In some applications, the DMSO may be formulated with lower boiling point diluents such as ethanol or water. For example, one liter of the DMSO-containing insecticidal formulation, in a specific embodiment, comprises 25 percent DMSO and 75 percent ethanol by volume, based on the total volume of the solution, with the insecticidal active ingredient(s) being added to such base solution of DMSO and ethanol. By specific choice of diluents, etc., the persistence of the DMSO-containing insecticidal formulation can be selectively varied, to achieve a particular character of cidal action on bed bugs in a specific environment. Other illustrative specific diluent species include water, isopropyl alcohol, acetone, methanol, and other DMSO-soluble and DMSO-miscible diluents that are effective to constitute formulations of the present disclosure, e.g., to vary the amount of DMSO that is applied to a specific locus.

It has been found that DMSO may be formulated with substantial amounts of diluents, cosolvents, etc., while retaining the effectiveness and advantages of DMSO in such reduced volume DMSO-containing formulations. Liquid insecticidal formulations containing as little as 0.1 percent by volume DMSO, based on the total volume of the formulation, in combination with other diluents, have been demonstrated to exhibit enhanced effectiveness for extended periods of time against bed bugs. In general, the duration of enhanced effectiveness of the bed bug-combating insecticidal formulation, in relation to corresponding formulations lacking DMSO therein, increases with increasing concentration of DMSO in the formulation.

Depending on the temperature conditions, the concentration of DMSO in the formulation and the application rate of the formulation, DMSO-containing formulations of the present disclosure, when applied to room temperature surfaces at 22° C., can remain in place for a week or more, with such applied material remaining wet to the touch for several days and thereafter persisting for up to a week in the form of a waxy residue on the surface after the liquid DMSO is gone. The waxy deposit also finally disappears, but the treated area exhibits a high degree of bed bug-combating character throughout the "liquid phase" and subsequent "waxy residue phase."

It will be recognized that the character and extent of persistence of the DMSO-containing insecticidal formulation can be readily varied by corresponding varying of the amounts of DMSO in the formulation and/or rates of application (i.e., amount of formulation applied per unit area) to the environment to be treated to combat bed bugs therein.

In DMSO-containing insecticidal formulations of the present disclosure, it has been found that the inclusion of ethanol in the formulation greatly enhances toxicity of various insecticidal formulations to bed bugs, particularly when the formulation is applied directly to them. Ethanol in such formulations may have the further benefit of a desiccating effect on bed bugs and may in combination with DMSO serve to enhance the overall rate and extent of penetration of the bed bug exoskeleton.

In various embodiments of the DMSO-containing insecticidal formulations of the present disclosure, insecticidal active ingredient(s) may be employed that are not highly soluble in DMSO and/or other diluents employed in the formulation, e.g., water. In such instance, the formulation may be constituted with any of various surfactants, emulsifiers and/or wetting agents, as necessary or appropriate to provide the insecticidal formulation with an appropriate character for application, and appropriate cidal activity for combating bed bug infestation.

DMSO-containing insecticidal formulations of the present disclosure may additionally incorporate any suitable ingredients that achieve or assist in achieving desirable characteristics of the formulation. Such additional ingredients may include, without limitation, stabilizers, antioxidants, thickeners or other viscosity control agents, colorants to aid the achievement of uniform application of the formulation, or any other ingredients, additives, adjuvants, or excipients that are beneficial as regards the character and performance of the formulation.

In various embodiments of the DMSO-containing insecticidal formulations of the present disclosure, one or more insecticidal active ingredient(s) may be employed. For example, insecticidal ingredients such as pyrethrins, deltamethrin, permethrin, chlorfenapyr, cyfluthrin, and imidacloprid, bifenthrin, fipronil, indoxacarb, abamectin, acetamiprid, fenvalerate, cypermethrin, cyhalothrin, hydroprene, etc., or combinations of such ingredients, may be employed in specific formulations. Such insecticidal active ingredients may be employed with or without insecticidal synergistic components (synergists), e.g., synergists such as piperonyl butoxide, N-octyl bicycloheptene dicarboximide (MGK264), etc.

Synergists improve the effectiveness of bed bug-combating insecticides by interfering with the detoxification of such insecticides in the body of the bed bug, thereby restoring at least some of the susceptibility of the bed bug to insecticides to which it otherwise may be resistant.

Insecticidal formulations containing DMSO and insecticidal active ingredient(s) can be formulated as concentrates, to which end users (applicators) can add further liquid diluent(s) such as water, prior to use. Alternatively, such formulations can be prepared in a ready-to-use format. In a specific embodiment, the insecticidal composition may be formulated as a concentrate that contains an insecticidal active ingredient, a synergist and DMSO, in addition to an emulsifier or surfactant to disperse the ingredients in the DMSO, and an end-user-added diluent. Formulations can be manufactured as ready-to-use formulations, containing the same ingredients as a final product composition made from a concentrate, after addition of water or other suitable diluent to complete the formulation for use.

In other embodiments of the present disclosure, DMSO is employed as a substitute diluent that is added to existing concentrate-form insecticidal formulations intended for use against bed bugs, in total or partial replacement of diluents that are otherwise prescribed for use with such concentrate formulations, to constitute the formulation for use. For example, DMSO can be used in an amount ranging from 0.1 percent to 100 percent of the diluent that is otherwise employed. In a specific implementation, DMSO can be used to replace some or all of the water normally added to an emulsifiable concentrate (EC) insecticide prior to use, for combating bed bugs. DMSO can also be included in emulsifiable water (EW) formulations.

It also has unexpectedly been found that DMSO alone, in the absence of any insecticidal active ingredient or synergist in the DMSO-containing formulation, is highly toxic to bed bugs upon contact with such formulation. DMSO shows toxicity resulting in mortality either when the bed bugs cross a surface to which DMSO has been applied and on which the formulation is still resident, i.e., it has not fully evaporated or sublimated, or when a DMSO-containing formulation is applied directly to the bed bug.

Importantly, it has been found that the toxic effect of DMSO against transiting bed bugs lasts for a considerable period of time after application of a DMSO-containing formulation to a surface, with a period of particularly heightened effectiveness of such applied formulation corresponding to the period during which some DMSO remains in liquid form on the target surface, and persisting at a high though somewhat reduced level of effectiveness during a period in which a post-liquid-drying waxy residue remains on the surface. Thus, the persistence of DMSO in remaining unevaporated form and subsequently in unsublimated form after administration, enables a high level of effectiveness to be achieved in the eradication of bed bugs.

It also has been unexpectedly found that DMSO alone, without an insecticidal active ingredient, can be diluted when a lower boiling point diluent (i.e., a diluent having a boiling point that is lower than that of DMSO) such as ethanol, and remains highly cidally effective against bed bugs, either when the mixture is directly applied to the bed bug or when the mixture is applied to a surface inhabited by bed bugs or on which bed bugs subsequently traverse. Such cidal activity against bed bugs has been found to remain high even after the lower boiling point diluent has evaporated.

The disclosure in various embodiments therefore contemplates DMSO-containing insecticidal formulations containing DMSO and a lower boiling point diluent, without any additional insecticidal active ingredient therein. Such "insecticidal active ingredient-free compositions" (such term referring here to compositions containing DMSO but free of any additional insecticidal active ingredient therein) are cidally effective against bed bugs, and thereby are characterized by superior safety in application and use.

It has been found that the cidal character of DMSO against bed bugs is not accompanied by any repellency effects, regardless of whether the DMSO-containing insecticidal formulation contains an additional insecticidal active ingredient or not, and regardless of the concentration of DMSO in the formulation. This is important, since any associated repellency would serve to substantially reduce actual contact of the bed bugs with the DMSO-containing formulation, by mediating avoidance behavior on the part of bed bugs in respect of environments to which the DMSO-based formulation has been applied.

Because essentially all insects have chitinous exoskeletons similar to that of the bed bug, the use of DMSO as an insecticidal formulation additive has broad applicability, in dramatically increasing the efficacy of many insecticidal formulations, against a wide range of insects. The disclosure therefore contemplates in other embodiments various methods of combating insect pests utilizing DMSO-containing formulations, including formulations containing additional insecticidal agent(s), as well as formulations containing DMSO alone.

Accordingly, while the disclosure herein is primarily directed to treatment and eradication of bed bugs, the use of DMSO as herein described is also highly effective in application to other insects, including insects that are characterized by limited routes of bioavailability (biological systemic susceptibility) to toxicants. Thus, DMSO alone, with or without additional insecticidal active ingredient(s), can also be used to kill insects by direct application to the insect or by application to an environment containing or susceptible to incursion of such insects.

Concerning bed bugs, DMSO-containing formulations in accordance with the present disclosure can be employed to kill bed bugs in a wide variety of circumstances, in a wide variety of implementations, and at a wide variety of locations. Surfaces susceptible to bed bug infestation that are treatable with DMSO-containing formulations of the present disclosure include: non-visible surfaces that are in an interior structure or otherwise out in plain sight; visible non-contact surfaces, which are not contacted or are not contacted with any frequency by humans or other animals; and visible contact surfaces, which come in contact with humans or other animals on a continuing basis.

In application to non-visible surfaces, the DMSO-containing insecticidal formulation is desirably constituted for extended cidal action, so that the wet phases and waxy residue phases of the applied formulation are maximized in temporal extent. Formulations for application to visible non-contact surfaces may be correspondingly constituted for either short-term or longer-term residual activity after initial application. Formulations for application to visible contact surfaces may be constituted to adjust the wet phase to a desired period of time consistent with the use of the surface or structure comprising same by humans or other animals.

In general, DMSO-containing insecticidal formulations of the present disclosure can be applied essentially anywhere that that bed bug infestation is occurring or can potentially occur, e.g., in host environments, such as beds, furniture (and components thereof that may harbor resting bed bugs, such as bed frames, mattresses, mattress tufts, bedsprings, headboards, etc.), carpets, flooring, vehicles including automotive vehicles, passenger train cars, and aircraft, cracks and crevasses between structural elements, in structural seams and joints, under rugs, inside and under furniture, inside and behind appliances, inside structural walls, below floors and above ceilings, behind wall hangings, or any other environments, surfaces, materials, articles, etc. that are susceptible to bed bug infestation. Surfaces contemplated for such application includes surfaces on which bed bugs transit between their resting areas and areas in which potential hosts reside or otherwise are present, as well as application to such resting areas and potential host areas themselves.

DMSO-containing insecticidal formulations of the present disclosure can be readily prepared by blending or mixing of their respective ingredients, and can be formulated for long residual presence, by formulation with correspondingly high percentages of DMSO, e.g., from 40% to 90% or more by volume, based on total volume of the insecticidal formulation containing such DMSO. In various embodiments, DMSO may be present as the only other ingredient, in combination with an insecticidal active ingredient, such as in formulations containing 0.01 to 10% insecticidal active ingredient by weight, based on weight of the formulation, with DMSO constituting the remainder of the formulation containing such insecticidal active ingredient, it being understood that the term "insecticidal active ingredient" when applied to formulations containing DMSO means an insecticidal active ingredient other than DMSO.

In specific applications, the DMSO-containing insecticidal formulations of the present disclosure can be formulated to remain in place and be cidally active for as long as a week or more.

In some instances, it may be desirable to apply DMSO-containing formulations to mattress resting surfaces in such manner that the mattress is left untouched for a period of time until all of the applied DMSO has evaporated. For example, a mattress surfaces can be treated with a DMSO-containing insecticidal formulation containing 0.05% by weight insecticidal active ingredient, 5% by weight DMSO, and the balance of the formulation being constituted by ethanol, wherein such percentages by weight are based on weight of the total formulation. The treatment formulation can be made up to provide a desired period of DMSO residual activity on the mattress surfaces, so as to kill any bed bugs traversing such surfaces for the desired period of time.

When treating surfaces such as mattress surfaces and human contact portions of any type of furniture or appliance, in which there is reason to avoid application of an insecticidal active ingredient, DMSO-containing formulations can take the form of low percentage compositions in which the amount of DMSO is 10% or less by volume, and a lower boiling solvent such as ethanol is present in a high percentage of 90% or more by volume, based on the total volume of the DMSO and lower boiling point solvent, wherein such formulation contains no additional insecticidal active ingredient. Such formulations avoid potential issues of the additional insecticidal active ingredients on human contact surfaces, and provide a suitably compact period of time during which the applied formulation is in the wet phase. Formulations of such type can be made up to dissipate in a period of hours to days after the application, depending on temperature of the application surface, the rate of application, and the specific amount of DMSO in the formulation.

In other embodiments, DMSO-containing insecticidal formulations of the present disclosure can be formulated with natural product active insecticidal ingredients and active insecticidal ingredients that are highly and rapidly biodegradable. For example, a natural pyrethrin insecticide, and a synergist such as piperonyl butoxide, could be utilized in DMSO-containing insecticidal formulations of the present disclosure.

In a further embodiment, a formulation containing 50% by volume DMSO and 50% by volume ethanol, based on total volume of such components, can be formulated with or without additional insecticidal active ingredients, as a bed bug-combating formulation useful for application to visible non-contact surfaces such as carpets under a bed.

DMSO-containing formulations of the present disclosure can be utilized in conjunction with bed bug attraction and entrapment methods and articles. Once a bed bug is attracted to a desired location or entrapped, it can be exterminated by contact with a DMSO-containing insecticidal formulation, either by direct contact with the formulation, or by contact with a treated surface, material or article to which the formulation has been applied.

For instance, the DMSO-containing insecticidal formulation can be used in conjunction with bed bug trapping cups placed under bed legs. In such applications the DMSO-containing formulation can be poured into and remain in such cups, so the bed bugs falling into the traps will be immediately immobilized and quickly killed by the DMSO component, when the formulation is free of other insecticidal active ingredients, or by the combination of the DMSO component and any additional insecticidal active ingredients formulated therewith, when the DMSO-containing formulation is so constituted. The DMSO component in any such formulations, due to its high boiling point, will remain in the cups for an extended period of time before the formulation needs to be replenished.

In addition to direct application of DMSO-containing liquid formulations, absorbents having a high affinity to DMSO can be impregnated or otherwise treated with DMSO-containing formulations of the present disclosure. The resulting DMSO formulation-containing absorbents can be located at strategic points, where bed bugs are expected to transit. Such absorbent placements may be hidden from view, or otherwise appropriately located, to provide an extended period of effectiveness of the DMSO-containing insecticidal formulation. The absorbent may for example be selected to slowly and steadily release the DMSO and other formulation components to its surface, for extended cidal action. For this purpose, sponges, cellulosic fibers, fibrous mats, molecular sieves, and the like, have potential utility as absorbent media for presentation of the DMSO-containing insecticidal formulation to the bed bug pests sought to be eradicated. Finished absorbent articles can be fabricated, e.g., in the form of small square or elongated strip articles comprising the DMSO-containing insecticidal formulation, and such absorbent articles can be provided with adhesive backings that can be utilized to positionally retain the absorbent article in place near bed bug harborages. DMSO-containing formulation-containing absorbent articles can be affixed, for example, to bed components such as frame and spring components, or otherwise on undersides or other surfaces of seating, such as in theaters, to kill bed bugs transiting across such structures in search of a host.

DMSO-containing insecticidal formulations of the present disclosure can be prepared in a variety of modified forms, such as sustained- or delayed-release formulations, to substantially extend the period during which DMSO is present in liquid form after application of the formulation to a surface. For example, DMSO can be microencapsulated so that DMSO and any additional insecticidal active ingredient present in the DMSO-containing formulation will be slowly released from the microcapsules onto the application surface. In other embodiments, agents such as propylene glycol can be added to DMSO-containing formulations to retard evaporation of DMSO from treated surfaces. Such formulation embodiments can substantially extend the period of time that DMSO is present on a treated surface, e.g., to several weeks.

Modifications can also be made to facilitate the use of DMSO-containing insecticidal formulations of the present disclosure in areas where the temperature is below or may drop below the melting/freezing point of DMSO. Addition of longer-lasting, lower melting point/higher boiling point cosolvents or diluents such as propylene glycol can be used to lower the freezing point of DMSO-containing insecticidal formulations, to facilitate their use in situations in which formulations are applied to surfaces or areas in which temperature is near or below the freezing point of DMSO. Because propylene glycol will remain resident at the application locus for a comparable period of time to DMSO, such modification enables the use of DMSO-containing liquid formulations in cooler areas, in which DMSO alone would normally be a solid.

DMSO-containing formulations of the present disclosure may also be formulated with substances or additives that further enhance penetration while retaining a suitably slow evaporation rate, to increase the bioavailability of toxicants to bed bugs and/or other insects.

Such enhancing agents include, without limitation, the substances listed as skin penetration enhancers in the article "Skin Penetration Enhancers Cited in the Technical Literature" in the November, 1997 issue of Pharmaceutical Technology. As a specific example, laurocapram (CAS#59227-89-3), commonly referred to as Azone, exhibits toxicity-enhancing characteristics similar to DMSO and may be used in addition to, or alternatively in place of, DMSO, in the insecticidal formulations.

Thus, the present disclosure in specific embodiments contemplates formulations containing DMSO, as a carrier, diluent, or solvent, alone or in combination with bed bug toxicants, and optionally in combination with lower boiling point diluents as well as other formulation ingredients. Insecticidal formulations of the present disclosure can be utilized in a variety of application environments, to achieve eradication of bed bugs and other insects in a simple and effective manner.

In specific aspects, the present disclosure relates to methods, compositions and articles as described below.

In one aspect, the disclosure relates to a method of combating bed bugs in a locus containing or susceptible to incursion of same, said method comprising applying to said locus and/or bed bugs therein a cidally effective amount of a formulation comprising dimethyl sulfoxide (DMSO).

In such method, the formulation can further comprise a bed bug toxicant. It can also, or alternatively comprise, a diluent, such as a lower boiling point diluent, e.g., a diluent selected from the group consisting of water, alcohols, ketones, aldehydes, ethers, and polyols. In other embodiments, the lower boiling point diluent comprises a diluent selected from the group consisting of water, isopropyl alcohol, acetone, and methanol. Ethanol is an advantageous lower boiling point diluent, and in one embodiment, the formulation comprises ethanol in an amount of from 0.5% to 99.5% by volume, based on total volume of DMSO and ethanol.

In another embodiment of the above-described method, the formulation contains from 0.1% to 100% DMSO by weight, based on weight of the formulation. In a still further embodiment, the formulation contains from 0.5% to 80% DMSO by weight, based on weight of the formulation.

The formulation in methods of the present disclosure may be constituted so as to be free of any additional insecticidal active ingredient, or alternatively, the formulation may comprise at least one additional insecticidal active ingredient. In the latter instance, the additional insecticidal active ingredient may comprise an insecticidal active ingredient selected from the group consisting of pyrethrins, deltamethrin, permethrin, chlorfenapyr, cyfluthrin, and imidacloprid, bifenthrin, fipronil, indoxacarb, abamectin, acetamiprid, fenvalerate, cypermethrin, cyhalothrin, and hydroprene. The formulation can further comprise a synergist, such as piperonyl butoxide or N-octyl bicycloheptene dicarboximide.

In the method as above described, the formulation can further comprise an additive selected from the group consisting of surfactants, emulsifiers and/or wetting agents. In other embodiments, the formulation further comprises an additive selected from the group consisting of stabilizers, antioxidants, thickeners, viscosity control agents, and colorants effective to aid the achievement of uniform application of the formulation.

Further specific embodiments include methods in which the formulation further comprises a solvent selected from the group consisting of water and alkanols. In another embodiment, the formulation further comprises water. In yet another embodiment, the formulation comprises DMSO, ethanol, and another insecticidal active ingredient. The formulation may be constituted in other embodiments as comprising an insecticidal synergist, and an insecticidal active ingredient for which the insecticidal synergist is synergistic.

Additional method embodiments include methods in which the formulation: comprises a pyrethrin; comprises at least one of bifenthrin and imidacloprid; comprises an enhancing agent effective to enhance persistence of the formulation after application, in relation to a corresponding formulation lacking such enhancing agent, e.g., a glycol enhancing agents such as propylene glycol.

The locus to which the method of the disclosure is applied can be of any suitable type, and may for example comprise a location on, in or near a site selected from the group consisting of bed frames, mattresses, mattress tufts, bedsprings, headboards, carpets, flooring, vehicles, aircraft, cracks and crevasses between structural elements, structural seams and joints, sites under rugs, sites inside and under furniture, sites inside and behind appliances, sites inside structural walls, sites below floors, sites above ceilings, and sites behind wall hangings. The formulation in the practice of the method may be applied to the locus in any suitable manner, e.g., by spraying, dipping or aerosol application. In a specific embodiment, the formulation can be applied to the locus in a container holding the formulation. In another embodiment, the formulation can be applied to the locus on or in an absorbent medium. The formulation in various embodiments may comprise a penetration enhancing agent, such as for example laurocapram.

Another aspect of the disclosure relates to a method of eradicating insects in a locus containing or susceptible to incursion of same, said method comprising applying to said locus and/or insects therein a cidally effective amount of a formulation comprising dimethyl sulfoxide (DMSO).

In a further aspect, the disclosure relates to a pesticidal composition comprising dimethyl sulfoxide (DMSO) and at least one of: (i) insecticidal ingredient(s) and (ii) diluent(s).

The pesticidal composition thus may comprise at least one additional insecticidal ingredient, e.g., a bed bug toxicant. In other embodiments, the pesticidal composition may comprise at least one diluent, e.g., a lower boiling point diluent such as a diluent selected from the group consisting of water, alcohols, ketones, aldehydes, ethers, and polyols. In specific embodiments, the lower boiling point diluent can comprise a diluent selected from the group consisting of water, isopropyl alcohol, acetone, and methanol. In a specific embodiment, the lower boiling point diluent comprises ethanol.

A specific pesticidal composition of the disclosure comprises ethanol in an amount of from 0.5% to 99.5% by volume, based on total volume of DMSO and ethanol. The composition may comprise any suitable amount of DMSO, such as an amount from 0.1% to 100% DMSO by weight, based on weight of the composition, or an amount from 0.5% to 80% DMSO by weight, based on weight of the composition. The composition may be free of any additional insecticidal active ingredient, or alternatively, it may contain at least one insecticidal ingredient. In a particular embodiment, the composition includes at least one insecticidal ingredient selected from the group consisting of pyrethrins, deltamethrin, permethrin, chlorfenapyr, cyfluthrin, and imidacloprid, bifenthrin, fipronil, indoxacarb, abamectin, acetamiprid, fenvalerate, cypermethrin, cyhalothrin, and hydroprene. The opposition may additionally comprise a synergist, such as piperonyl butoxide or N-octyl bicycloheptene dicarboximide.

The composition in other specific embodiments may include: an additive selected from the group consisting of surfactants, emulsifiers and/or wetting agents; an additive selected from the group consisting of stabilizers, antioxidants, thickeners, viscosity control agents, and colorants effective to aid the achievement of uniform application of the formulation; a solvent selected from the group consisting of water and alkanols; water; DMSO, ethanol, and another insecticidal active ingredient; an insecticidal synergist, and an insecticidal active ingredient for which the insecticidal synergist is synergistic; a pyrethrin; bifenthrin and/or imidacloprid; an enhancing agent effective to enhance persistence of the composition after application, in relation to a corresponding composition lacking such enhancing agent, e.g., a glycol such as propylene glycol; an absorbent medium; or a penetration enhancing agent such as laurocapram.

Another aspect of the disclosure relates to an absorbent article comprising an absorbent body and DMSO absorbed on and/or in said absorbent body.

Such adsorbent article may further comprise an adhesive disposed on said absorbent body, for adhesively affixing the absorbent article to a surface or structure. The adsorbent article also can comprise at least one of: (i) insecticidal ingredient(s) and (ii) diluent(s) absorbed with said DMSO on and/or in said absorbent body.

The advantages and features of the compositions and methods of the present disclosure are further illustrated with reference to the following examples, which are not to be construed as in any way limiting the scope of the invention but rather as illustrative of various embodiments in specific implementations of the disclosure.

Example 1

Toxicity and Durability of Toxicity of DMSO against Bed Bugs (Diluted and Undiluted)

Example 1A 0.1 milliliters of Fisher Biotech Molecular Biology Grade 99.7% DMSO (CAS#67-68-5) was applied to each of five 3.5 cm diameter disks of Fisherbrand Qualitative P8 filter paper. Immediately after application of the DMSO to the filter papers, each individual filter paper was laid in the bottom of a 4.5 cm diameter clear plastic jar as the arena for testing, with a screw-on lid. Each lid had a ventilation hole drilled in its top portion, over which was glued a plastic mesh screen. 10 bed bugs were deposited on the filter paper in each of the five arenas, after which the lids of the respective jars were screwed on the corresponding jars. One identically configured control arena with a blank untreated filter paper on the bottom and containing 10 bed bugs was also assembled without any DMSO being applied to the filter paper prior to its being placed in the arena. The arenas were placed in an incubator set to maintain a temperature of 22° C.

At the end of 24 hours, timed from the initial placement of the bed bugs on the filter papers, all of the arenas were removed from the incubator and opened and the bed bugs were examined. All of the bed bugs in all 5 of the jars containing DMSO treated filter paper were dead. The bed bugs in the control jar were all still alive.

Without removing the filter paper, the dead bed bugs in the 5 arenas were removed and replaced by the same number (10) of live bed bugs in each arena. The arenas were again placed in the incubator and re-examined 24 hours later. The replacement bed bugs in the 5 arenas were also all dead.

Three more replications (three more successive removals of dead bed bugs and replacement with live bed bugs in each of the five treated arenas at 24 hour intervals) were performed with all bed bugs found to be dead upon examination at the end of each 24 hour interval (for a total of 5 replications). All of the bed bugs in the control jar were all still alive at the end of the last testing interval.

The results of such testing demonstrated the ability of DMSO to kill bed bugs. The results also demonstrated the durability of the toxic action of DMSO against bed bugs over several days (successive 24 hour periods).

Example 1B 0.1 milliliters of a mixture of 75% ethanol and 25% DMSO (by volume) was applied to five 3.5 cm diameter disks of filter paper. After application of the mixture to the filter papers, each filter paper disk was allowed to dry for three hours in order to allow the ethanol to evaporate while leaving higher boiling point DMSO in place. Each individual filter paper disk was then laid in the bottom of a 4.5 cm. diameter clear plastic jar (arena). 10 bed bugs were deposited on the filter paper in each of the five arenas and vented lids were screwed on. One additional control arena with an ethanol only treated filter paper (with the ethanol also being allowed to dry) on the bottom and containing 10 bed bugs was also assembled. All of the arenas were placed in the incubator under the same conditions as used in Example 1A. The ethanol was allowed to dry before placement of the bed bugs, since it has the potential to kill bed bugs alone by desiccation or exoskeleton penetration, and its function in this particular test was as a diluent of the DMSO and not as a toxicant or penetrant.

After 24 hours all of the bed bugs were dead. The dead bed bugs were removed and replaced with live bed bugs 4 more successive times (for a total of 5) at 24 hour intervals, with the same results (all bed bugs dead) at the end of each 24 hour inspection interval. The filter paper was barely wet to the touch at the end of the final replication.

These results demonstrate the durability of the action of DMSO against bed bugs even when the amount of DMSO in a formulation is substantially reduced by its replacement or dilution with a lower boiling point solvent.

Example 2

Speed of Toxic Action of DMSO Against Bed Bugs 0.1 milliliters of DMSO was applied to five 3.5 cm. diameter circular pieces of filter paper. Each individual filter paper was laid in the bottom of a 4.5 cm diameter clear plastic jar (arena). 10 bed bugs were deposited on the filter paper in each of the five arenas and the lid (providing for aeration) was screwed on. One additional control arena with a blank untreated filter paper on the bottom and containing 10 bed bugs was also assembled, without any DMSO being applied to the filter paper prior to its placement in the arena. All of the arenas were placed inside the incubator. The arenas were inspected at 3, 6, and 12 hours after initial placement of the bed bugs on the filter paper.

The number of dead bed bugs at each inspection time interval after their placement on the filter papers is set out in the tabulation listing of Table 1.

TABLE 1

| DMSO only | Arena 1 | Arena 2 | Arena 3 | Arena 4 | Arena 5 | Control |
|---|---|---|---|---|---|---|
| 3 hours | 2 | 3 | 1 | 2 | 1 | 0 |
| 6 hours | 5 | 7 | 8 | 4 | 8 | 0 |
| 12 hours | 10 | 10 | 10 | 10 | 10 | 0 |

The data in Table 1 demonstrate the speed with which DMSO can kill bed bugs.

Example 3

Enhanced Toxicity and Acceleration of the Speed of Toxic Action of an Insecticidal Active Ingredient when Combined with DMSO Example 3A 0.5 gram of bifenthrin (CAS #82657-04-3) and 0.5 grams of imidacloprid (CAS #138261-41-3) were mixed in 1 liter of ethanol until they were in solution. This amount of bifenthrin and imidacloprid in ethanol is equivalent to a 0.13% w/w solution of these two insecticides in ethanol. 0.1 milliliters of this insecticide-containing solution was applied to each of 5 filter papers. The ethanol was allowed to dry from the filter papers for one hour, after which the filter papers were placed into five arenas. 10 bed bugs then were placed into the five arenas on top of the filter paper. One additional control arena with an ethanol only treated filter paper on the bottom and containing 10 bed bugs was also assembled, without any insecticide being applied to the filter paper prior to its placement in the arena. The ethanol was allowed to dry from all arenas for the same reasons as described in Example 1B. All the arenas were placed in the incubator and remained there except during inspections.

The bed bugs in all the arenas were examined at 3, 6, 12, 24, 48, and 72 hours after initial placement on the filter papers. The number of dead bed bugs at each inspection time interval after their placement on the filter papers is set out in the tabulation listing of Table 2.

TABLE 2

| Bifenthrin/ Imidacloprid | Arena 1 | Arena 2 | Arena 3 | Arena 4 | Arena 5 | Control |
|---|---|---|---|---|---|---|
| 3 hours | 0 | 0 | 1 | 0 | 0 | 0 |
| 6 hours | 0 | 1 | 1 | 1 | 0 | 0 |
| 12 hours | 2 | 1 | 2 | 1 | 2 | 0 |
| 24 hours | 3 | 2 | 3 | 2 | 2 | 1 |
| 48 hours | 4 | 5 | 6 | 3 | 4 | 1 |
| 72 hours | 4 | 6 | 6 | 6 | 4 | 1 |

The data in Table 2 demonstrated the difficulty of killing bed bugs when they reside on a surface to which an insecticide has been applied as part of a liquid solution and all of the liquid carrier has evaporated.

Example 3B

One liter of a 75% ethanol and 25% DMSO mixture by volume was prepared, to which was added 0.5 grams of bifenthrin and 0.5 grams of imidacloprid. The mixture was stirred until the insecticides were in solution. This amount of bifenthrin+imidacloprid in ethanol+DMSO is equivalent to a 0.115% w/w solution of the insecticides in the two liquids. 0.1 milliliters of the solution was applied to each of five 3.5 millimeter diameter filter paper disks. The filter papers were allowed to dry for three hours (to flash off the ethanol with extra time allowed for the ethanol to completely separate from the DMSO which it was miscible) after which the filter papers were placed into the five arenas on top of which 10 bed bugs were placed. One additional control arena with an ethanol treated filter paper on the bottom and containing 10 bed bugs was also assembled without any insecticide or DMSO being applied to the filter paper prior to its placement in the arena. The ethanol was allowed to dry for all arenas for the same reasons as discussed in Example 1B. Except during times of inspection, the arenas remained in the incubator.

The bed bugs in all 5 arenas were examined after 3, 6, and 12 hours. The number of dead bed bugs at each inspection time interval after their placement on the filter papers is set out in the tabulation listing of Table 3.

TABLE 3

| Bifenthrin/ Imidacloprid plus DMSO and ethanol | Arena 1 | Arena 2 | Arena 3 | Arena 4 | Arena 5 | Control |
|---|---|---|---|---|---|---|
| 3 hours | 6 | 5 | 4 | 5 | 7 | 0 |
| 6 hours | 8 | 7 | 7 | 10 | 9 | 0 |
| 12 hours | 10 | 10 | 10 | X | 10 | 0 |

X = all bed bugs died before this inspection

A comparison of the results of Example 3A and 3B demonstrates the ability of DMSO to greatly enhance the speed with which insecticides act on bed bugs.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure is intended to be broadly construed and interpreted, as including all such variations, modifications and alternative embodiments, within its spirit and scope.

What is claimed is:

1. A method of combating bed bugs in a locus, said method comprising applying to said locus and/or bed bugs therein a cidally effective amount of a formulation comprising dimethyl sulfoxide (DMSO), wherein the formulation is free of any additional insecticidal active ingredient.

2. The method of claim 1, wherein the formulation further comprises a diluent.

3. The method of claim 2, wherein the diluent has a lower boiling point than DMSO.

4. The method of claim 3, wherein the diluent is selected from the group consisting of water, alcohols, ketones, aldehydes, and ethers.

5. The method of claim 3, wherein the diluent is selected from the group consisting of water, isopropyl alcohol, acetones, and methanol.

6. The method of claim 3, wherein the diluent is ethanol.

7. The method of claim 6, wherein the formulation comprises ethanol in an amount of from 0.5% to 99.5% by volume, based on total volume of DMSO and ethanol.

\* \* \* \* \*